United States Patent
Dickinson et al.

(10) Patent No.: US 8,439,963 B2
(45) Date of Patent: May 14, 2013

(54) APPARATUS AND METHOD FOR MAINTAINING FLUID FLOW THROUGH BODY PASSAGES

(75) Inventors: Robert Julian Dickinson, London (GB);
Andrew Robert Pacey, Herts (GB);
Martin Terry Rothman, London (GB);
Ajay Kumar Jain, London (GB)

(73) Assignee: LimFlow GmbH, Dresden (DE)

( * ) Notice: Subject to any disclaimer, the term of this patent is extended or adjusted under 35 U.S.C. 154(b) by 443 days.

(21) Appl. No.: 12/297,498

(22) PCT Filed: Apr. 20, 2007

(86) PCT No.: PCT/GB2007/001430
§ 371 (c)(1),
(2), (4) Date: Feb. 25, 2009

(87) PCT Pub. No.: WO2007/122396
PCT Pub. Date: Nov. 1, 2007

(65) Prior Publication Data
US 2009/0306755 A1     Dec. 10, 2009

(30) Foreign Application Priority Data
Apr. 20, 2006  (GB) .................................. 0607761.4

(51) Int. Cl.
*A61F 2/82* (2006.01)

(52) U.S. Cl.
USPC ......... 623/1.13; 623/1.15; 623/1.16; 606/108

(58) Field of Classification Search .................. 623/1.14, 623/1.11, 1.15, 1.2, 1.18, 1.36
See application file for complete search history.

(56) References Cited

U.S. PATENT DOCUMENTS

| | | | | |
|---|---|---|---|---|
| 5,591,226 A | * | 1/1997 | Trerotola et al. | 623/1.12 |
| 5,639,278 A | * | 6/1997 | Dereume et al. | 623/1.13 |
| 5,720,776 A | * | 2/1998 | Chuter et al. | 623/1.36 |
| 5,951,599 A | | 9/1999 | McCrory | |
| 6,190,353 B1 | | 2/2001 | Makower et al. | |
| 6,287,336 B1 | | 9/2001 | Globerman et al. | |

(Continued)

FOREIGN PATENT DOCUMENTS

| | | |
|---|---|---|
| WO | WO 00/09041 | 2/2000 |
| WO | WO 00/33770 | 6/2000 |
| WO | 2005065579 A1 | 7/2005 |

OTHER PUBLICATIONS

U.S. Appl. No. 11/662,128, Minimally Invasive Surgical Apparatus and Methods, filed Jan. 3, 2008.

(Continued)

*Primary Examiner* — Thomas J Sweet
*Assistant Examiner* — Jason-Dennis Stewart
(74) *Attorney, Agent, or Firm* — Knobbe Martens Olson & Bear LLP

(57) ABSTRACT

A device (10) for maintaining fluid flow through at least one passage in a human or animal body, the device comprising two end portions (12, 14) for anchoring the device in position, and an intermediate portion (16) which allows movement of the end portions relative to each another, wherein the end portions and intermediate portion together define a pathway for fluid flow through the device. The device is particularly suitable for use in the treatment of coronary heart disease by minimally invasive surgery, and the invention extends to a method for diverting fluid flow from one passage to another.

52 Claims, 4 Drawing Sheets

U.S. PATENT DOCUMENTS

| | | | |
|---|---|---|---|
| 6,863,684 B2 | 3/2005 | Kim et al. | |
| 7,582,108 B2 | 9/2009 | Hierlemann et al. | |
| 7,670,329 B2 | 3/2010 | Flaherty et al. | |
| 7,780,719 B2 | 8/2010 | Killion et al. | |
| 7,849,860 B2 | 12/2010 | Makower et al. | |
| 7,966,057 B2 | 6/2011 | Macaulay et al. | |
| 2001/0041930 A1 | 11/2001 | Globerman et al. | |
| 2004/0199243 A1* | 10/2004 | Yodfat | 623/1.16 |
| 2005/0165469 A1* | 7/2005 | Hogendijk | 623/1.15 |
| 2008/0009936 A1 | 1/2008 | Kim et al. | |
| 2010/0094391 A1 | 4/2010 | Heraty et al. | |
| 2011/0054589 A1 | 3/2011 | Bashiri et al. | |
| 2011/0251671 A1 | 10/2011 | Heraty et al. | |
| 2011/0319902 A1 | 12/2011 | Epstein | |

OTHER PUBLICATIONS

U.S. Appl. No. 12/297,498, Apparatus and Method for Maintaining Fluid Flow Through Body Passages, filed Feb. 25, 2009.

* cited by examiner

APPARATUS AND METHOD FOR MAINTAINING FLUID FLOW THROUGH BODY PASSAGES

The present invention relates to apparatus and methods for use in percutaneous interventional surgery. In particular, the invention relates to a device for maintaining fluid flow through passages such as blood vessels.

Minimally invasive percutaneous surgery, commonly known as 'key-hole' surgery, is a well-known surgical technique wherein surgical devices are inserted into a patient's body through a small aperture cut. For example, it is often preferable to use key-hole surgery in cardiovascular procedures, so as to avoid the substantial discomfort, trauma, high risk of infection and long recovery time typically associated with conventional surgery.

Key-hole surgery is often used in the treatment of coronary heart disease, in which a coronary artery is partially occluded by a blockage such as an atheroma. For example, in balloon angioplasty, a balloon catheter comprising a flexible, hollow tube is inserted into an artery, usually near the patient's groin, and is guided through the body to the patient's heart. The heart and the cardiac arteries may be visualised using X-ray fluoroscopy, and the tip of the catheter may be fluorescent so that its position can be determined. The catheter carries an inflatable balloon near its distal tip. The balloon is positioned in or near to the blockage, and then the balloon is inflated so as to widen or dilate the occluded blood vessel to restore blood flow through the coronary artery to the cardiac tissue.

A tubular supporting device or stent may be deployed at the site of the blockage to prevent future occlusion (restenosis) or collapse of the blood vessel. The stent may, for example, be an expandable metal mesh tube which is carried on the balloon of the balloon catheter. While on the catheter, the tube has a relatively small diameter in comparison to the diameter of the blood vessel. The stent expands when the balloon is inflated, so that the stent pushes against the wall of the blood vessel. The stent is arranged to retain its expanded shape when it reaches its expanded position, for example by plastic deformation or by means of a mechanical locking mechanism, so as to form a resilient scaffold or support in the blood vessel. The stent supports and dilates the wall of the blood vessel to maintain a pathway for blood to flow through the vessel. Self-expanding stents are also available, which are held in a collapsed state by a suitably adapted catheter for transport through the artery and which adopt an expanded state when deployed at the site of the blockage. The catheter may, for example, comprise a retaining sleeve which retains the stent in a compressed or unexpanded state. Upon removal or withdrawal of the sleeve from the stent, the stent expands to support and dilate the wall of the blood vessel.

In acute cases of coronary heart disease, where a coronary artery is severely or completely occluded, angioplasty may not be suitable. Instead, coronary bypass surgery may be required. Bypass surgery is an open-chest or open-heart procedure, and typically involves grafting a piece of healthy blood vessel onto the coronary artery so as to bypass the blockage and restore blood flow to the coronary tissue. The healthy blood vessel is usually a vein harvested from the patient's leg or arm during the course of the bypass operation. To perform the procedure, the patient's heart must be exposed by opening the chest, separating the breastbone, and cutting the pericardium surrounding the heart, resulting in significant surgical trauma.

Certain patients are unsuitable as candidates for conventional coronary bypass surgery, due to the significant trauma, high risk of infection and long recovery time associated with open-chest surgery. For example, factors such as diabetes, age, obesity and smoking may exclude patients who are in need of treatment.

It is therefore desirable to provide new and improved apparatus and methods for use in minimally invasive surgical procedures, so that the need to perform conventional surgery to treat conditions such as coronary heart disease may be reduced. In this way, patients who might otherwise be unable to receive surgery such as coronary bypass surgery can be treated, and in all cases the amount of surgical trauma, the risk of infection and the time to recovery could be significantly reduced in comparison to conventional open-chest surgery.

Improved methods and apparatus for performing procedures such as coronary bypass by minimally invasive surgical techniques are described in the present applicant's published international patent application no. WO-A-2006/027599, the contents of which is hereby incorporated into this specification by reference. In particular, techniques for effectively bypassing an occlusion in a coronary artery by percutaneous surgery are described. These techniques involve creating a channel or passage between the coronary artery upstream of the occlusion and a coronary vein adjacent to the coronary artery to interconnect the artery and the vein. Arterial blood is diverted from the coronary artery into the coronary venous system by way of the interconnecting passage, and the arterial blood can perfuse the cardiac tissue in a retrograde manner (retroperfusion). In this way, the occlusion in the artery is effectively bypassed.

The interconnecting passage between the artery and vein is created by, for example, deploying a needle outwards from a first catheter located within the artery, so that the needle traverses the interstitial tissue or septum between the artery and the vein. A second catheter may be provided and located in the vein, so as to provide a target device which receives a signal, for example an ultrasound signal, transmitted from the first catheter. By monitoring the received signal, the position of the first catheter with respect to the second catheter can be determined so as to ensure that the needle is deployed in the correct position and orientation to create a passage for fluid flow between the artery and the vein.

In order to maintain the flow of blood thorough the interconnecting passage, a tube or similar structure may be inserted in the passage to support the interstitial tissue and prevent the passage from closing. The tube may for example be an expandable stent which is deployed in the channel using a balloon catheter, as previously described. The balloon catheter may be guided to the channel by a guide wire deployed in the passage by the first catheter.

The artery and vein pulsate as the heart beats, due to the movement of the heart wall and fluctuations in pressure within the blood vessels themselves. This pulsation causes movement of the vessels relative to each another, which imposes a cyclic stress on the stent disposed within the interconnecting passage. This cyclic stress is relatively large in comparison to that experienced by a stent disposed within a single blood vessel. This cyclic stress can lead to premature failure of the stent, for example by fatigue failure of the stent struts. Failure of the stent may result in injury to the interstitial tissue and occlusion of the interconnecting passage, which could lead to significant complications or complete failure of the therapy.

Against this background, the present invention aims to provide improved apparatus and methods for maintaining fluid flow in passages such as blood vessels and surgically-created openings. The apparatus and methods of the invention are suitable for use in minimally invasive surgical techniques.

Accordingly, in a first aspect the invention provides a device for maintaining fluid flow through at least one passage in a human or animal body, the device comprising two end portions for anchoring the device in position, and an intermediate portion which allows movement of the end portions relative to each another, the end portions and intermediate portion together defining a pathway for fluid flow through the device.

By allowing the two end portions to move relative to each other, the device can respond to movement of the passage or passages in which the device is used. The intermediate portion may be flexible to allow relative movement of the end portions. Expressed in another way, the device has varying or differential flexibility along its length. The likelihood of device failure due to fatigue is reduced as a result of the flexibility, because the magnitude of stresses within the intermediate portion is relatively low in comparison to a stent with uniform flexibility along its length.

The device may be capable of maintaining fluid flow through a single passageway, for example an occluded blood vessel. Advantageously, the intermediate portion may be capable of maintaining fluid flow between two passages that can be interconnected by the intermediate portion passing through a further passage extending between the two passages. In this way, the device is suitable for use as a shunt between two passages, for example between an artery and a vein.

Because the end portions can move relative to one another by virtue of the intermediate portion, the device is suitable for use in applications where the end portions are anchored in separate passages which move relative to one another. By means of the invention, a pathway for fluid communication is maintained through the device irrespective of the relative movement of the end portions, and the likelihood of fatigue failure of the device due to cyclic movement of the end portions is low in comparison to a conventional stent which does not have an intermediate portion.

Advantageously, the end portions are diametrically expandable to anchor the device in position. An expanded end portion may, for example, be expandable to meet with and press against the walls of a passage to prevent substantial sliding or rotation of the end portion within the passage, and to dilate the passage. The intermediate portion may be diametrically expandable to dilate the fluid flow pathway.

The device may be in the form of a tube defining a lumen which acts as the fluid flow pathway. In one embodiment of the invention, the tube may be fluid-tight, so as to confine the fluid flow within the lumen of the tube. The tube is preferably made from a polymeric material, for example a biocompatible polymer such as PTFE or polyurethane.

The device may include a supporting structure that supports the end portions. The supporting structure may also support the intermediate portion, in which case the supporting structure may be flexible within the intermediate portion to allow movement of the end portions relative to each other.

When a supporting structure is provided, the supporting structure or a portion thereof may be embedded within a wall of the tube. Alternatively or in addition, the structure or a portion of the structure may be located on the outside of the tube or within the lumen of the tube.

The supporting structure may be in the form of at least one mesh. For example, a single mesh may be provided which extends along the length of the device. In another example, a mesh is provided at each end portion of the device, in which case the meshes may stop short of the intermediate portion or may extend into the intermediate portion. When a mesh is present in the intermediate portion, the mesh may have a higher density (that is, a smaller spacing between filaments of the mesh) in the end portions than in the intermediate portion so that the device is relatively more flexible in the intermediate portion than in the end portions.

At least one mesh may be of biocompatible metal wire. For example, the metal wire may be stainless steel. Alternatively, or in addition, at least one mesh is of a shape memory material, for example nitinol. When a shape memory material is used, at least a portion of the device may be self-expanding.

One or both end portions may be provided with anchoring barbs. The barbs are capable of digging into or grasping the inside wall of a passage so as to prevent or reduce slippage or other movement of the or each end portion relative to the passage.

The two end portions may have different diameters, so that the device can be made to fit securely within a passage having variable diameter, or with one end portion in a first passage and the other end portion in a second passage, when the passages have different diameters. In this way, the device can be optimised for a particular application or for a particular patient.

In a second aspect, the invention resides in a method of diverting fluid flow from a first passage to an adjacent second passage in a human or animal body. The method includes forming a third passage between the first and second passages; providing a device having two end portions and an intermediate portion, for maintaining fluid flow; deforming the intermediate portion of the device to permit insertion of the device in the passages; and expanding the end portions against the walls of the first and second passages so as to anchor the device in the passages. For example, the intermediate portion of the device may be flexed to permit insertion of the device in the passages.

One or more end portions of the device may be expanded by a balloon catheter. Alternatively, or in addition, at least one end portion may be self-expanding, in which case the method may include providing the device in a retaining sleeve, and removing the retaining sleeve to enable the at least one end portion to expand.

The method may further include expanding the intermediate portion to dilate the third passage, thus allowing a larger pathway for fluid flow from the first passage to the second passage.

The method of the invention may be used in many surgical procedures, and can be performed by minimally invasive (key-hole) techniques. The method is particularly suitable for the treatment of coronary heart disease, by providing a shunt or bypass to divert arterial blood from an occluded coronary artery to an adjacent coronary vein.

To this end, in a third aspect, the present invention extends to a method of treating coronary heart disease, the method including diverting arterial blood from a coronary artery to a coronary vein by the method of the second aspect of the invention.

Specific embodiments of the invention will now be described by reference to the accompanying drawings, in which like reference numerals are used for like features and in which.

Figure 1:
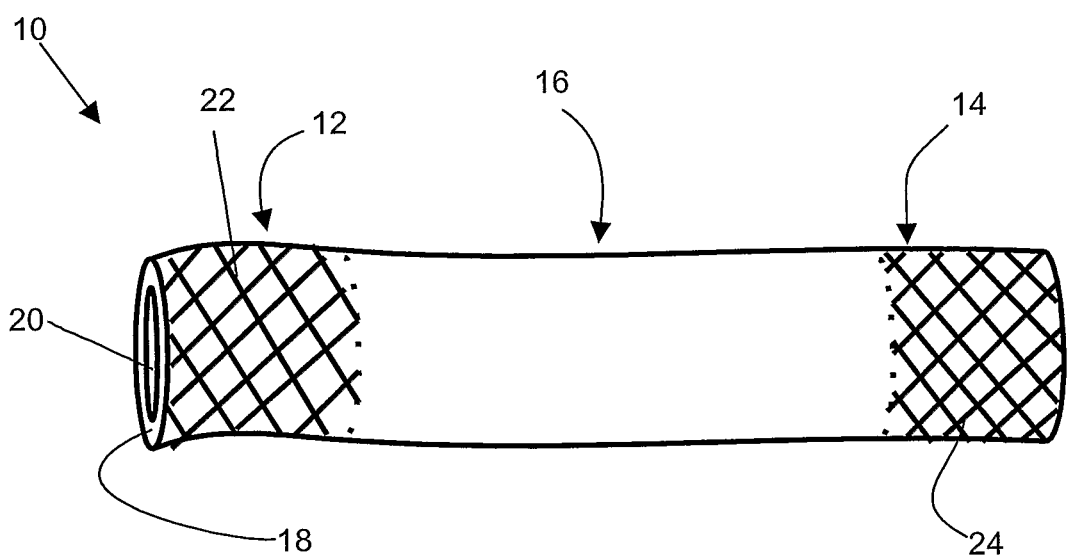
FIG. 1 shows a stent according to a first embodiment of the present invention.

In the embodiment of the invention shown in FIG. 1, there is provided a device for maintaining fluid flow through at least one passage, comprising a stent 10 having a first or proximal end portion 12, a second or distal end portion 14, and an intermediate portion 16 between the proximal and distal end portions 12, 14. The stent 10 is formed from a flexible polymer tube 18, which defines a bore or lumen 20 for passage of fluid through the stent 10.

A support structure comprising a stainless steel wire mesh 22 is embedded in the outside wall of the tube 18 within the proximal end portion 12 of the stent 10. Likewise, a stainless steel wire mesh 24 is embedded in the outside wall of the tube 18 within the distal end portion 14 of the stent 10. The intermediate portion 16, which lies between the proximal and distal end portions 12, 14, does not include a wire mesh.

The wire meshes 22, 24 within the end portions 12, 14 stiffen the stent 10 in the end portions 12, 14. In this way, the intermediate portion 16 is relatively flexible in comparison to the end portions 12, 14, and the end portions 12, 14 have a relatively high radial stiffness.

The end portions 12, 14 of the stent 10 are diametrically expandable. In this first embodiment of the invention, the wire meshes 22, 24 are formed so that, after manufacture of the stent 10, the end portions 12, 14 of the stent 10 have a smaller diameter than the passages, for example blood vessels, into which the stent 10 will be deployed. When the stent 10 is in position in the passages, the end portions 12, 14 can be expanded or deformed outwardly so that the respective diameters of the end portions 12, 14 increase. In this way, the end portions 12, 14 meet with and push against the walls of the passages. The end portions 12, 14 are arranged to maintain the expanded diameter indefinitely, for example by plastic deformation of the wire of the meshes 22, 24 or by provision of a locking mechanism arranged to mechanically lock the mesh 22, 24 in its expanded position.

The intermediate portion 16 of the stent 10 is also diametrically expandable, for example by way of plastic deformation of the tube 18.

Figure 2:
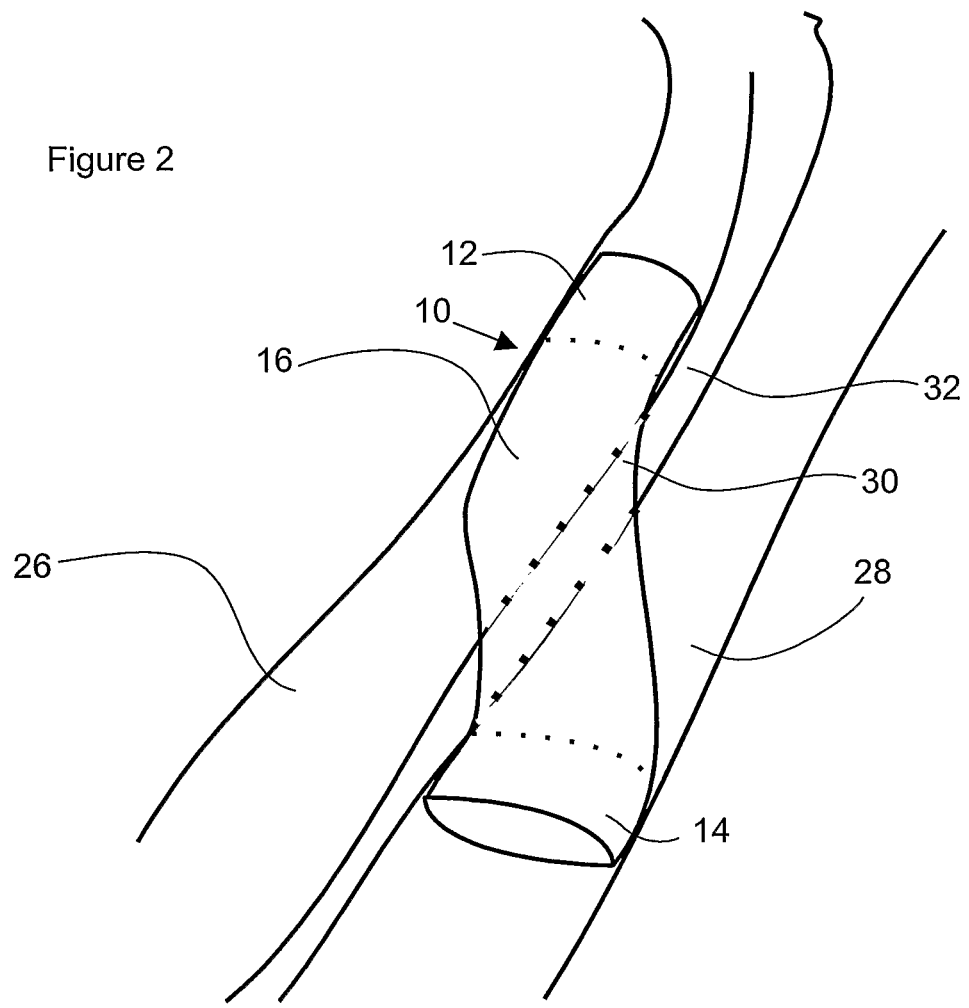
FIG. 2 shows the stent of FIG. 1, in use as a shunt between two adjacent blood vessels.

FIG. 2 shows the stent 10 of FIG. 1 deployed to maintain a fluid flow path between two passages comprising blood vessels, namely a coronary artery 26 and a coronary vein 28. The end portions 12, 14 and the intermediate portion 16 of the stent 10 have been expanded to meet with and push against the inner walls of the blood vessels 26, 28. The distal end portion 14 of the stent 10 is located within the vein 28, and the proximal end portion 12 of the stent 10 is located within the artery 26. The intermediate portion 16 extends through an opening or interconnecting passage 30 surgically formed between the artery 26 and the vein 28.

The expanded end portions 12, 14 of the stent 10 are resilient, and impart an outward radial force on the inner walls of the blood vessels 26, 28. By virtue of the radial stiffness of the end portions 12, 14 of the stent 10, the end portions 12, 14 are held or anchored in place within the respective blood vessels 26, 28. Slippage of the stent 10 within the blood vessels 26, 28 is thereby prevented or reduced. In this way, the end portions 12, 14 of the stent 10 serve to anchor or fix the stent 10 in position, in use, while maintaining fluid flow through the lumen 20 of the tube 18. In this way, the stent 10 acts as a shunt between the artery 26 and the vein 28.

The intermediate portion 16 of the stent 10 has substantial flexibility, so that the intermediate portion 16 can conform to the 'S' shape formed by the artery 26, the vein 28 and the interconnecting passage 30 in combination. Furthermore, the flexible intermediate portion 16 allows the end portions 12, 14 of the stent 10 to move with respect to one another in response to relative movement of the artery 26 and the vein 28.

Because the intermediate portion 16 does not include a wire mesh but is instead made from the flexible polymer material of the tube 18, the intermediate portion 16 is not susceptible to damage due to fatigue if relative movement of the blood vessels 26, 28 imparts a cyclic stress to the stent 10.

The intermediate portion 16 of the stent 10 has sufficient resilience to maintain dilatation of the interconnecting passage 30, so that the interconnecting passage 30 remains open for blood flow from the artery 26 to the vein 28 by way of the lumen 20 of the tube 18. Blood flow from the artery 26 to the vein 28, by way of the interconnecting passage 30, is therefore maintained through the lumen 20 of the tube 18. In other words, the stent 10 supports the artery 26, the vein 28, and the interconnecting passage 30 to maintain a pathway for fluid communication through the stent 10.

The proximal and distal end portions 12, 14 of the stent 10 are arranged so that, when the stent 10 is deployed with its distal end portion 14 in a vein 28 and its proximal end portion 12 in an artery 26 as shown in FIG. 2, the diameter of the expanded distal end portion 14 is sufficient to hold the distal end portion 14 within the vein 28, and likewise the diameter of the expanded proximal end portion 12 is sufficient to hold the proximal end portion 12 within the artery 26. The diameter of the proximal end portion 12 may therefore differ from the diameter of the distal end portion 14. By selecting appropriate diameters for the end portions 12, 14 and the intermediate portion 16, the stent 10 can be tailored to the anatomy of an individual patient.

A procedure for positioning the stent of FIG. 1 to provide a shunt between an occluded coronary artery 26 and an adjacent coronary vein 28 in order to achieve reteroperfusion of arterial blood to the heart, as shown in FIG. 2, will now be described.

Using standard procedures that will be familiar to those skilled in the art, a catheter is inserted into the patient's arterial system by way of a small aperture cut, usually in the patient's groin area. The catheter is fed to the artery 26 and guided to a position upstream of the site of the occlusion and where a vein 28 lies close to and substantially parallel to the artery 26. A hollow needle is deployed from the catheter and inserted through the wall of the coronary artery 26, through the interstitial tissue 32 which separates the artery 26 and vein 28, and through the wall of the vein 28. The path of the needle creates an interconnecting passage or opening 30 to allow blood flow between the artery 26 and the vein 28.

Before the needle is withdrawn, a guide wire is inserted through the hollow needle and into the vein 28. The needle is then retracted, leaving the guide wire in place. The catheter carrying the needle can then be withdrawn from the patient's body. The guide wire can be used to guide further catheters to the interconnecting passage 30 between the artery 26 and the vein 28.

The stent 10 is initially provided in a non-expanded state and is carried towards the interconnecting passage 30 on a balloon catheter, guided by the guide wire. The distal end portion 14 of the stent 10 is passed through the interconnecting passage 30 and into the vein 28, leaving the proximal end portion 12 in the artery 26. The intermediate portion 16 of the stent 10 flexes to adopt a curved or 'S'-shaped formation, so that the intermediate portion 16 extends through the interconnecting passage 30.

The balloon catheter is adapted to expand the proximal end portion 12 of the stent 10 upon inflation of a balloon, so as to increase the diameter of the proximal end portion 12 and anchor the proximal end portion 12 against the inner wall of the artery 26. Likewise, the balloon catheter is adapted to expand the distal end portion 14 of the stent 10 upon inflation of a balloon, so as to anchor the distal end portion 14 against the inner wall of the vein 28. The balloon catheter is also adapted to expand the intermediate portion 16 of the stent 10, so that the interconnecting passage 30 can be widened or dilated as far as necessary to obtain sufficient blood flow from the artery 26 to the vein 28.

After the end portions 12, 14 of the stent 10 have been expanded, the balloon catheter and the guide wire are withdrawn from the patient's body. In this way, the stent 10 is anchored or fixed in position within the vein 28, artery 26 and the interconnecting passage 30 as shown in FIG. 2.

The balloon catheter may be adapted to selectively expand the proximal end portion 12, distal end portion 14 and intermediate portion 16 of the stent 10 individually or in combination, for example by the provision of two or more separately inflatable balloons or balloon portions. Alternatively, a single balloon may be provided so as to expand all of the portions of the stent 10 simultaneously.

Other steps may be included in the procedure. For example, before the stent 10 is deployed, a balloon catheter may be guided to the interconnecting passage 30 and positioned so that an inflatable balloon portion of the catheter lies in the interconnecting passage 30. Upon inflation of the balloon, the balloon pushes against the walls of the interconnecting passage 30 to widen or dilate the interconnecting passage 30 to ease subsequent insertion of the stent.

Figure 3:
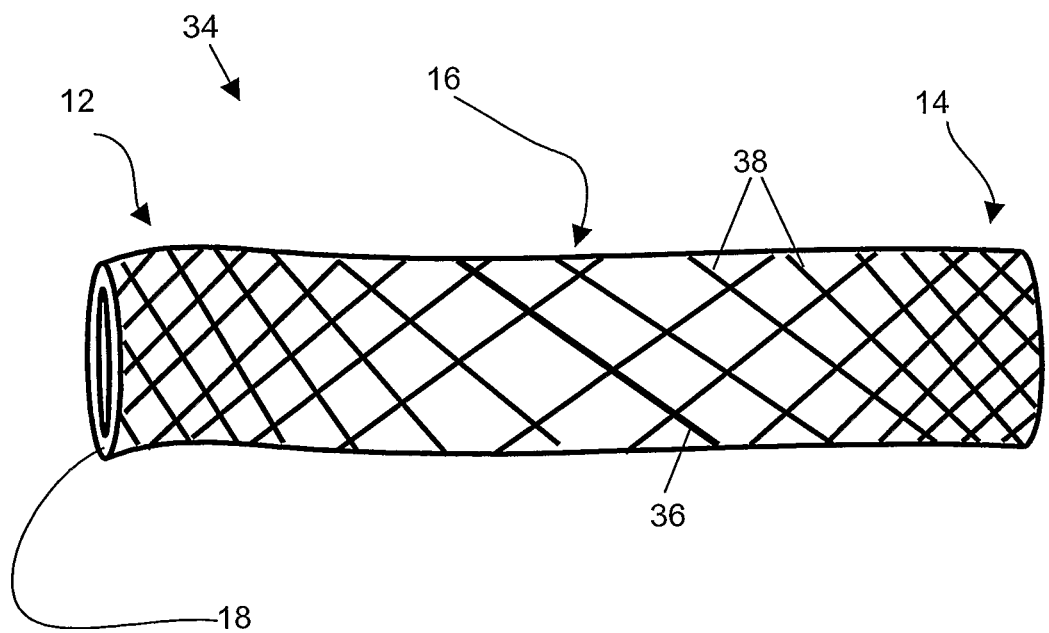
FIG. 3 shows a stent according to a second embodiment of the present invention.

In a second embodiment of the invention, shown in FIG. 3, a stent 34 is provided which includes a support structure comprising a wire mesh 36 formed by winding wire in a lattice configuration around a polymer tube 18. As in the first embodiment, the stent 34 comprises a proximal end portion 12, a distal end portion 14, and an intermediate portion 16. In this embodiment, the wire mesh 36 extends along the whole length of the stent 34, including the intermediate portion 16.

The wire mesh 36 is arranged so that the spacing between the filaments 38 of the mesh 36 is relatively small at the proximal and distal end portions 12, 14 of the stent 34, while the spacing between the filaments 38 is relatively large in the intermediate portion 16 of the stent 34. In other words, the winding density of the mesh 36 is relatively low in the intermediate portion 16 of the stent 34, and relatively high in the end portions 12, 14 of the stent 34. In this way, the intermediate portion 16 of the stent 34 is relatively flexible in comparison to the end portions 12, 14. Although the wire mesh 36 in the intermediate portion 16 may be subject to cyclic stress, in use, the relatively high flexibility of the intermediate portion 16 due to the low winding density means that the magnitude of the cyclic stress is low. The risk of fatigue failure of the stent 34, and particularly the filaments 38 of the mesh 36, is therefore reduced in comparison to a conventional stent having uniform flexibility along its length.

Figure 4:
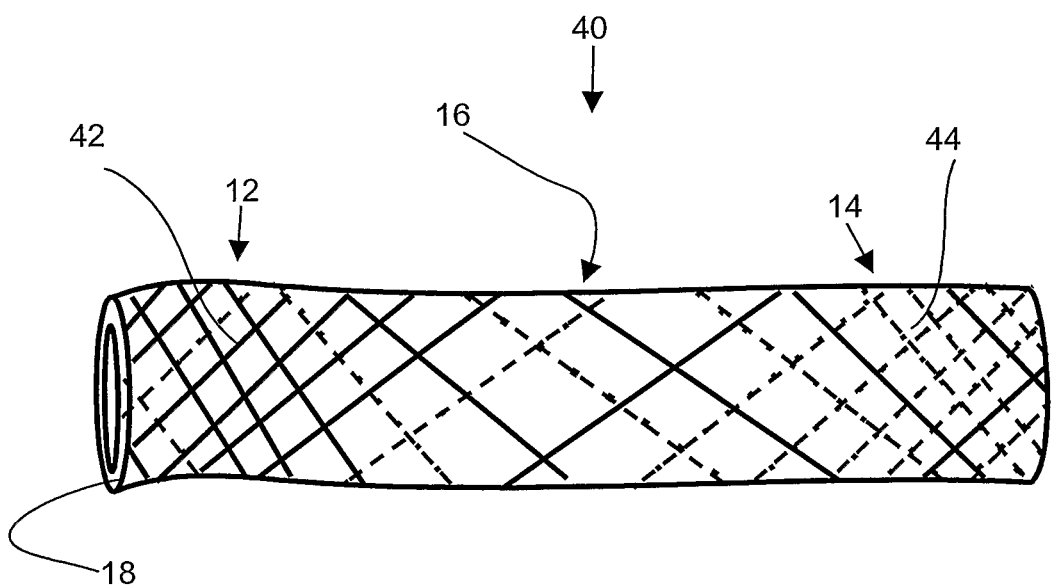
FIG. 4 shows a stent according to a third embodiment of the present invention.

In a third embodiment of the invention, shown in FIG. 4, there is provided a stent 40 comprising a polymer tube 18 around which is formed a support structure comprising a first wire mesh 42 and a second wire mesh 44. The meshes 42, 44 are formed by winding wire in a lattice configuration around the polymer tube 18, and the first and second meshes 42, 44 are made from different materials. The first wire mesh 42 extends from the proximal end portion 12 of the stent 40 into the intermediate portion 16 of the stent 40. The second wire mesh 44 extends from the distal end portion 14 of the stent 40 into the intermediate portion 16 of the stent 40. In both cases, the winding density of the mesh 42, 44 is relatively high in the end portions 12, 14, and decreases in density towards the intermediate portion 16. In this way, the total winding density (i.e. the winding density of both meshes, taken together) is lower in the intermediate portion 16 than in the end portions 12, 14 of the stent 40, so that the intermediate portion 16 is relatively flexible in comparison to the end portions 12, 14.

Because the first and second meshes 42, 44 are made from different materials, the properties of each of the respective distal and proximal end portions 12, 14 of the stent 40 can be optimised for the particular application of the stent 40. For example the second mesh 44 at the distal end portion 14 of the stent 40 may be made from a relatively flexible metallic alloy for ease of insertion through an interconnecting passage between two blood vessels, while the first mesh 42 at the proximal end portion 12 of the stent 40 may be made from a relatively inelastic metallic alloy, so as to provide a high degree of resilience at the proximal end portion 14 to anchor the stent 40 firmly in position. It will be appreciated that the first and second meshes 42, 44 could instead be made from wires having the same material composition but with different wire diameter (gauge).

It will be appreciated that several modifications and variations of the invention are possible, some of which will now be described by way of example only.

The stent may be self-expanding. For example, the wire mesh may be made from a shape-memory material, such as nitinol, which is capable of returning to a manufactured shape after undergoing significant deformation. In this case, the stent is manufactured to have the shape that is required in the expanded configuration, and is compressed to fit inside a sleeve for transport on a catheter to the desired location. To deploy and expand the stent, the sleeve is drawn back from the stent to allow the shape memory material to return to its manufactured shape, to anchor the stent and dilate the passages. The use of a balloon catheter is therefore not required when the stent is self-expanding.

It is also envisaged that a stent may be provided which comprises one or more self-expanding portions, and one or more portions which are expandable by deformation, for example using a balloon catheter. For example, in the embodiment shown in FIG. 4, the first mesh may be made from stainless steel for expansion by a balloon catheter, and the second mesh may be made from nitinol for self-expansion upon deployment of the stent.

In any embodiment of the invention, the polymer tube may be made from any suitable compliant or flexible polymer, such as PTFE or polyurethane. In some applications, for example when the stent is to be deployed within a single blood vessel, a tube need not be provided. In such cases, the intermediate portion of the stent may for example comprise a wire mesh with a low winding density, while the end portions of the stent comprise a wire mesh with a higher winding density. The mesh is generally tubular to define a pathway for fluid flow through the centre of the mesh.

The wire mesh may be made from any suitable material, such as nitinol or stainless steel as previously described. The mesh need not be metal, but could instead be made from filaments of biodegradable or biocompatible polymer or glass. Different materials may be used for portions of the mesh, for example as previously described with reference to FIG. 4. Similarly, in the first embodiment of the invention, the wire mesh at the distal end portion and the wire mesh at the proximal end portion need not be made from the same material.

Although a wire mesh has been described, any other structure which supports the stent and provides the necessary degree of resilience may be used in place of a wire mesh. For example, a laser-perforated metal tube may be used alone or in combination with a polymer tube. The perforations of the metal tube are arranged so as to provide a relatively flexible intermediate portion and relatively stiff end portions of the stent. The supporting structure may instead be an open-cell foam disposed within the tube.

In one variation, the stent comprises a polymer tube, and no supporting structure is provided. Instead, the intermediate portion of the stent is made relatively more flexible than the end portions by decreasing the wall thickness of the polymer tube within the intermediate portion.

When a wire mesh or other supporting structure is provided in combination with a polymer tube, the supporting structure may be located around the outside of the tube, in the inner bore of the tube, or embedded within a wall of the tube. It is conceivable that more than one supporting structure may be provided, in which case each supporting structure may have a different location with respect to the tube.

One or both of the end portions of the stent may be provided with means for anchoring the stent to the walls of the passage or passages in which those ends are located. For example, the end portions of the stent may be provided with anchoring means comprising hooks or barbs arranged to grasp or grip the passage wall.

It will be appreciated that there need not be a well-defined transition between the intermediate and end portions of the stent. Instead, the flexibility of the stent may increase gradually when moving from an end portion towards the intermediate portion. Such an arrangement is exemplified by the second and third embodiments of the invention described with reference to FIGS. 3 and 4.

While the device of the present invention is particularly suitable for use as a transvascular shunt in coronary surgery, it will be appreciated that the device could be used in many other medical applications. For example, the device could be used in angioplasty for the treatment of occluded blood vessels with tortuous or kinked paths, or where the vessels may be subject to significant deflection or deformation at or near the position of the stent. The stent could also be used for the repair of damaged blood vessels, for example in aortic grafting procedures. In these cases, the flexible intermediate portion of the stent allows the stent to conform to the shape of a blood vessel and to readily deform in response to movement of the vessel without the risk of fatigue failure, while remaining fixed or anchored in position by virtue of the relatively stiff end portions.

While it is anticipated that the device of the present invention will be used most often in applications where the fluid that flows through the stent is a liquid such as blood, it is conceivable that the device could be used in applications such as tracheal or bronchial surgery where the fluid is a gas, such as air. In other applications, the fluid may contain solid matter.

The invention claimed is:

1. A device for maintaining fluid flow through at least one passage in a human or animal body, the device comprising first and second end portions for anchoring the device in position, and an intermediate portion therebetween, the end portions and intermediate portion being in the form of a tube that defines a lumen which acts as a pathway for fluid flow through the device, wherein the tube is made from a polymeric material and further comprises a first wire mesh and a second wire mesh, the first wire mesh extending from the first end portion of the device into the intermediate portion of the device, the second wire mesh extending from the second end portion into the intermediate portion of the device, wherein the winding density of the first and second wire meshes is relatively high in the first and second end portions but is lower in the intermediate portion so that the first and second end portions have high radial stiffness relative to the intermediate portion, wherein at least a portion of the first and second wire mesh is embedded within a wall of the tube; and wherein the intermediate portion is flexible relative to the end portions such that, in use of the device, the intermediate portion allows the first and second end portions to move relative to one another in response to movement of the at least one passage.

2. The device of claim 1, wherein the device is capable of maintaining fluid flow between a first passage and an adjacent second passage, through an intermediate passage, such that the first end portion is anchored in the first passage, the second end portion is anchored in the second passage, and the intermediate portion passes through the intermediate passage thereby allowing relative movement of the first and second end portions in response to relative movement of the first and second passages.

3. The device of claim 2, wherein the first passage is substantially parallel to the second passage.

4. The device of claim 2, wherein the intermediate portion is conformable to an "S" shape formed by the first passage, the second passage, and the intermediate passage in combination.

5. The device of claim 1, wherein the end portions are diametrically expandable to anchor the device in position.

6. The device of claim 1, wherein the intermediate portion is diametrically expandable to dilate the fluid flow pathway.

7. The device of claim 1, of which at least one of the portions is self-expanding.

8. The device of claim 1, wherein the end portions are provided with anchoring barbs.

9. The device of claim 1, wherein the end portions have differing diameters.

10. A method of diverting fluid flow from a first passage to an adjacent second passage in a human or animal body, the method including:
forming a third passage between the first and second passages;
providing a device having first and second end portions and an intermediate portion, for maintaining fluid flow, the end portions and intermediate portion being in the form of a tube that defines a lumen which acts as a pathway for fluid flow through the device, wherein the tube is made from a polymeric material and further comprises a first wire mesh and a second wire mesh, the first wire mesh extending from the first end portion of the device into the intermediate portion of the device, the second wire mesh extending from the second end portion into the intermediate portion of the device, wherein the winding density of the first and second wire meshes is relatively high in the first and second end portions but is lower in the intermediate portion so that the first and second end portions have high radial stiffness relative to the intermediate portion, and the intermediate portion being flexible relative to the end portions such that, in use of the device, the intermediate portion allows the first and second end portions to move relative to one another;
deforming the intermediate portion of the device to permit insertion of the device in the passages; and
expanding the first and second end portions against the walls of the first and second passages respectively so as to anchor the device in the passages.

11. The method of claim 10, wherein the end portions are expanded by a balloon catheter.

12. The method of claim 10, wherein at least one end portion is self-expanding, the method including providing the device in a retaining sleeve, and removing the retaining sleeve to enable the at least one end portion to expand.

13. The method of claim 10, further including expanding the intermediate portion to dilate the third passage.

14. The method of claim 10, wherein the first passage is substantially parallel to the second passage.

15. The method of claim 10, wherein the intermediate portion is conformable to an "S" shape formed by the first passage, the second passage, and the intermediate passage in combination.

16. A method of treating coronary heart disease, the method including:
   diverting arterial blood from a coronary artery to a coronary vein by forming a passage between the artery and the vein;
   providing a device having first and second end portions and an intermediate portion, for maintaining fluid flow, the first and second end portions and intermediate portion being in the form of a tube that defines a lumen which acts as a pathway for fluid flow through the device, wherein the tube is made from a polymeric material and further comprises a first wire mesh and a second wire mesh, the first wire mesh extending from the first end portion of the device into the intermediate portion of the device, the second wire mesh extending from the second end portion into the intermediate portion of the device, wherein the winding density of the first and second wire meshes is relatively high in the first and second end portions but is lower in the intermediate portion so that the first and second end portions have high radial stiffness relative to the intermediate portion, and the intermediate portion being flexible relative to the end portions such that, in use of the device, the intermediate portion allows the first and second end portions to move relative to one another;
   deforming the intermediate portion of the device to permit insertion of the device in the artery, the vein and the passage; and
   expanding the first and second end portions against the walls of the artery and vein so as to anchor the device in the passages.

17. The method of claim 16, wherein the end portions are expanded by a balloon catheter.

18. The method of claim 16, wherein at least one end portion is self-expanding, the method including providing the device in a retaining sleeve, and removing the retaining sleeve to enable the at least one end portion to expand.

19. The method of claim 16, further including expanding the intermediate portion to dilate the third passage.

20. The method of claim 16, wherein the first passage is substantially parallel to the second passage.

21. The method of claim 16, wherein the intermediate portion is conformable to an "S" shape formed by the first passage, the second passage, and the intermediate passage in combination.

22. A device for maintaining fluid flow through at least one passage in a human or animal body, the device comprising first and second end portions for anchoring the device in position, and an intermediate portion therebetween, the end portions and intermediate portion being in the form of a tube that defines a lumen which acts as a pathway for fluid flow through the device, wherein the tube is made from a polymeric material and further comprises a first wire mesh and a second wire mesh, the first wire mesh extending from the first end portion of the device into the intermediate portion of the device, the second wire mesh extending from the second end portion into the intermediate portion of the device, wherein the winding density of the first and second wire meshes is relatively high in the first and second end portions but is lower in the intermediate portion so that the first and second end portions have high radial stiffness relative to the intermediate portion, wherein at least a portion of the first and second wire mesh is located on the outside of the tube;
   and wherein the intermediate portion is flexible relative to the end portions such that, in use of the device, the intermediate portion allows the first and second end portions to move relative to one another in response to movement of the at least one passage.

23. The device of claim 22, wherein the device is capable of maintaining fluid flow between a first passage and an adjacent second passage, through an intermediate passage, such that the first end portion is anchored in the first passage, the second end portion is anchored in the second passage, and the intermediate portion passes through the intermediate passage thereby allowing relative movement of the first and second end portions in response to relative movement of the first and second passages.

24. The device of claim 23, wherein the first passage is substantially parallel to the second passage.

25. The device of claim 23, wherein the intermediate portion is conformable to an "S" shape formed by the first passage, the second passage, and the intermediate passage in combination.

26. The device of claim 22, wherein the end portions are diametrically expandable to anchor the device in position.

27. The device of claim 22, wherein the intermediate portion is diametrically expandable to dilate the fluid flow pathway.

28. The device of claim 22, of which at least one of the portions is self-expanding.

29. The device of claim 22, wherein the end portions are provided with anchoring barbs.

30. The device of claim 22, wherein the end portions have differing diameters.

31. A device for maintaining fluid flow through at least one passage in a human or animal body, the device comprising first and second end portions for anchoring the device in position, and an intermediate portion therebetween, the end portions and intermediate portion being in the form of a tube that defines a lumen which acts as a pathway for fluid flow through the device, wherein the tube is made from a polymeric material and further comprises a first wire mesh and a second wire mesh, the first wire mesh extending from the first end portion of the device into the intermediate portion of the device, the second wire mesh extending from the second end portion into the intermediate portion of the device, wherein the winding density of the first and second wire meshes is relatively high in the first and second end portions but is lower in the intermediate portion so that the first and second end portions have high radial stiffness relative to the intermediate portion, wherein at least a portion of the first and second wire mesh is located within the lumen of the tube;
   and wherein the intermediate portion is flexible relative to the end portions such that, in use of the device, the intermediate portion allows the first and second end portions to move relative to one another in response to movement of the at least one passage.

32. The device of claim 31, wherein the device is capable of maintaining fluid flow between a first passage and an adjacent second passage, through an intermediate passage, such that the first end portion is anchored in the first passage, the second end portion is anchored in the second passage, and the intermediate portion passes through the intermediate passage thereby allowing relative movement of the first and second end portions in response to relative movement of the first and second passages.

33. The device of claim 32, wherein the first passage is substantially parallel to the second passage.

34. The device of claim 32, wherein the intermediate portion is conformable to an "S" shape formed by the first passage, the second passage, and the intermediate passage in combination.

35. The device of claim 31, wherein the end portions are diametrically expandable to anchor the device in position.

36. The device of claim 31, wherein the intermediate portion is diametrically expandable to dilate the fluid flow pathway.

37. The device of claim 31, of which at least one of the portions is self-expanding.

38. The device of claim 31, wherein the end portions are provided with anchoring barbs.

39. The device of claim 31, wherein the end portions have differing diameters.

40. A device for maintaining fluid flow through at least one passage in a human or animal body, the device comprising first and second end portions for anchoring the device in position, and an intermediate portion therebetween, the end portions and intermediate portion being in the form of a tube that defines a lumen which acts as a pathway for fluid flow through the device, wherein the tube is made from a polymeric material and further comprises a first wire mesh and a second wire mesh, the first wire mesh extending from the first end portion of the device into the intermediate portion of the device, the second wire mesh extending from the second end portion into the intermediate portion of the device, wherein the winding density of the first and second wire meshes is relatively high in the first and second end portions but is lower in the intermediate portion so that the first and second end portions have high radial stiffness relative to the intermediate portion, wherein the first and second wire mesh comprises a material selected from one or more of the group consisting of:
- a biocompatible metal, and
- a shape memory material;
- and wherein the intermediate portion is flexible relative to the end portions such that, in use of the device, the intermediate portion allows the first and second end portions to move relative to one another in response to movement of the at least one passage.

41. The device of claim 40, wherein the shape memory material is nitinol.

42. The device of claim 40, wherein at least a portion of the first and second wire mesh is embedded within a wall of the tube.

43. The device of claim 40, wherein at least a portion of the first and second wire mesh is located on the outside of the tube.

44. The device of claim 40, wherein at least a portion of the first and second wire mesh is located within the lumen of the tube.

45. The device of claim 40, wherein the device is capable of maintaining fluid flow between a first passage and an adjacent second passage, through an intermediate passage, such that the first end portion is anchored in the first passage, the second end portion is anchored in the second passage, and the intermediate portion passes through the intermediate passage thereby allowing relative movement of the first and second end portions in response to relative movement of the first and second passages.

46. The device of claim 45, wherein the first passage is substantially parallel to the second passage.

47. The device of claim 45, wherein the intermediate portion is conformable to an "S" shape formed by the first passage, the second passage, and the intermediate passage in combination.

48. The device of claim 40, wherein the end portions are diametrically expandable to anchor the device in position.

49. The device of claim 40, wherein the intermediate portion is diametrically expandable to dilate the fluid flow pathway.

50. The device of claim 40, of which at least one of the portions is self-expanding.

51. The device of claim 40, wherein the end portions are provided with anchoring barbs.

52. The device of claim 40, wherein the end portions have differing diameters.

* * * * *